(12) United States Patent
Oguni et al.

(10) Patent No.: US 12,080,104 B2
(45) Date of Patent: Sep. 3, 2024

(54) CLASSIFICATION METHOD

(71) Applicant: Semiconductor Energy Laboratory Co., Ltd., Atsugi (JP)

(72) Inventors: Teppei Oguni, Atsugi (JP); Takahiro Fukutome, Atsugi (JP)

(73) Assignee: Semiconductor Energy Laboratory Co., Ltd., Atsugi (JP)

( * ) Notice: Subject to any disclaimer, the term of this patent is extended or adjusted under 35 U.S.C. 154(b) by 282 days.

(21) Appl. No.: 17/637,563

(22) PCT Filed: Sep. 1, 2020

(86) PCT No.: PCT/IB2020/058111
§ 371 (c)(1),
(2) Date: Feb. 23, 2022

(87) PCT Pub. No.: WO2021/048682
PCT Pub. Date: Mar. 18, 2021

(65) Prior Publication Data
US 2022/0277591 A1    Sep. 1, 2022

(30) Foreign Application Priority Data

Sep. 12, 2019   (JP) .................................. 2019-166161

(51) Int. Cl.
*G06V 40/18*   (2022.01)
*G06T 7/60*    (2017.01)
(Continued)

(52) U.S. Cl.
CPC .............. *G06V 40/197* (2022.01); *G06T 7/60* (2013.01); *G06V 10/56* (2022.01); *G06V 10/764* (2022.01);
(Continued)

(58) Field of Classification Search
CPC .... G06V 40/197; G06V 10/56; G06V 40/193; G06V 10/774; G06V 10/764; G06T 7/60;
(Continued)

(56) References Cited

U.S. PATENT DOCUMENTS 5,573,006 A     11/1996  Shimotani et al.
7,620,218 B2 *  11/2009  Steinberg ............. G06V 40/161
                                                      382/103
(Continued)

FOREIGN PATENT DOCUMENTS

CN    101686815 A    3/2010
CN    104780834 A    7/2015
(Continued)

OTHER PUBLICATIONS

International Search Report (Application No. PCT/IB2020/058111) Dated Nov. 24, 2020.
(Continued)

*Primary Examiner* — William D Titcomb
(74) *Attorney, Agent, or Firm* — Eric J. Robinson; Robinson Intellectual Property Law Office, P.C.

(57) ABSTRACT

Person's conditions are classified according to his/her eye data. Person's conditions are classified according to his/her eye data using an imaging device, a feature extraction unit, and a classifier. The imaging device has a function of generating a group of images by continuous image capturing, and the group of images preferably includes an image of an eye area. The eye includes a black area and a white area. The method includes the steps in which the feature extraction unit extracts the eye area from the group of images, extracts a blinking amplitude, detects an image for determining start of eye blinking, stores an image for determining end of eye blinking as first data, and stores an image after a predetermined time elapsed from the first data (Continued)

as second data. The step in which the feature extraction unit extracts the white area from the first data and the second data is included. The classifier can use the white area as learning data.

5 Claims, 9 Drawing Sheets

(51) Int. Cl.
    *G06V 10/56*     (2022.01)
    *G06V 10/764*     (2022.01)
    *G06V 10/774*     (2022.01)
(52) U.S. Cl.
    CPC .......... *G06V 10/774* (2022.01); *G06V 40/193* (2022.01); *G06T 2207/10016* (2013.01); *G06T 2207/20081* (2013.01); *G06T 2207/30201* (2013.01)
(58) Field of Classification Search
    CPC . G06T 2207/10016; G06T 2207/20081; G06T 2207/3021
    USPC ......................................................... 381/117
    See application file for complete search history.

(56) References Cited

U.S. PATENT DOCUMENTS

| | | | | |
|---|---|---|---|---|
| 7,953,251 | B1* | 5/2011 | Steinberg | G06F 18/00 382/117 |
| 8,503,800 | B2* | 8/2013 | Blonk | G06F 18/214 382/226 |
| 8,790,280 | B2 | 7/2014 | Sakamoto et al. | |
| 9,984,299 | B2 | 5/2018 | Mori | |
| 10,445,881 | B2* | 10/2019 | Spizhevoy | G06V 10/764 |
| 10,552,693 | B2 | 2/2020 | Mori | |
| 11,610,311 | B2* | 3/2023 | Boyd | G06T 7/0014 |
| 2008/0317379 | A1* | 12/2008 | Steinberg | H04N 9/8042 382/275 |
| 2010/0191156 | A1 | 7/2010 | Sakamoto et al. | |
| 2011/0194738 | A1* | 8/2011 | Choi | G06V 40/197 382/117 |
| 2015/0238087 | A1 | 8/2015 | Yamashita et al. | |
| 2016/0106358 | A1 | 4/2016 | Macknik et al. | |
| 2017/0236016 | A1 | 8/2017 | Mori | |
| 2018/0137335 | A1 | 5/2018 | Kim et al. | |
| 2018/0235531 | A1 | 8/2018 | Macknik et al. | |
| 2018/0247141 | A1 | 8/2018 | Mori | |
| 2019/0223983 | A1* | 7/2019 | Mah | G06F 18/24323 |
| 2021/0279874 | A1* | 9/2021 | Boyd | A61B 5/0013 |
| 2022/0207729 | A1* | 6/2022 | Boyd | G06V 10/774 |
| 2023/0316522 | A1* | 10/2023 | Boyd | G16H 30/40 382/130 |

FOREIGN PATENT DOCUMENTS

| | | |
|---|---|---|
| CN | 106960199 A | 7/2017 |
| EP | 2918225 A | 9/2015 |
| EP | 3206162 A | 8/2017 |
| JP | 07-249197 A | 9/1995 |
| JP | 5718493 | 5/2015 |
| JP | 2015-132783 A | 7/2015 |
| JP | 2016-523112 | 8/2016 |
| JP | 2017-143889 A | 8/2017 |
| KR | 2013-0043366 A | 4/2013 |
| WO | WO-2009/001558 | 12/2008 |

OTHER PUBLICATIONS

Written Opinion (Application No. PCT/IB2020/058111) Dated Nov. 24, 2020.
Hoshino.K et al., "Estimation of Mental Fatigue through Analysis of Pupillary Light Response", The Journal of Institute of Television Engineers of Japan, May 20, 1995, vol. 49, No. 5, pp. 657-664.
Bradley.M et al., "The pupil as a measure of emotional arousal and autonomic activation", Psychophysiology, Jul. 1, 2008, vol. 45, No. 4, pp. 602-607.
Lee.E et al., "Measuring the degree of eyestrain caused by watching LCD and PDP devices", International Journal of Industrial Ergonomics, Sep. 1, 2009, vol. 39, No. 5, pp. 798-806.
Pang.L et al., "The techniques of studying normal blink reflex", Journal of Practical Stomatology, Sep. 1, 2009, No. 5, pp. 733-736.
Bour.L et al., "Neurophysiological Aspects of Eye and Eyelid Movements During Blinking in Humans", Journal of Neurophysiology, 2000, vol. 83, No. 1, pp. 166-176.

* cited by examiner

CLASSIFICATION METHOD

TECHNICAL FIELD

One embodiment of the present invention is a classification device and a classification method that classify person's conditions according to eye data.

One embodiment of the present invention relates to a method for generating a classifier that can classify person's conditions according to his/her eye data using a computer device. Another embodiment of the present invention relates to a method for generating learning data for learning eye data. Another embodiment of the present invention relates to a method for extracting an eye area from a group of images continuously captured by an imaging device, and extracting a feature amount from eye data obtained from the eye area. Another embodiment of the present invention relates to a method for training a classifier by supplying the classifier with the feature amount as learning data.

BACKGROUND ART

A social need to improve the quality of life has been increased in recent years. For example, overwork conditions or symptoms of mental illness are difficult to be recognized by oneself. If own conditions can be detected early, appropriate measures (such as resting) can be taken before the conditions worsen. For example, a way to self-check changes that he or she is not aware of is being researched as self-counseling.

Emotions, psychological conditions, or physical fatigue are known to manifest oneself in physical responses such as eye movements, facial expressions, voice, and heartbeat. The measurement of these physical responses will probably notify a person of changes in him/herself that he or she is not aware of. Thus, various studies have been conducted on eyes as elements that represent emotions, psychological conditions, or physical fatigue. This is because the eyes directly receive an instruction from the brain, which controls the mind part of a person. Data that can be obtained by analyzing changes appearing in the eyes (hereinafter referred to as eye data) is considered to be an important factor also for studying the brain.

The eye data can be obtained from an image taken by an imaging device, which does not disturb a person's movement or work. As an example of self-counseling method, a study of detecting sleepiness, which is a form of physical fatigue, from pupil changes has been conducted. For example, Patent Document 1 discloses a detection method of determining a pupil state from an eye image captured using an infrared ray, thereby determining a person's condition.

Patent Document 2 discloses a system for detecting a neurological disease by detecting microsaccades, which are a form of eyeball movement.

REFERENCE

Patent Document

[Patent Document 1] Japanese Published Patent Application No. H07-249197
[Patent Document 2] Japanese Translation of PCT International Application No. 2016-523112

SUMMARY OF THE INVENTION

Problems to be Solved by the Invention

One of the method of obtaining eye data is an EOG (electrooculogram) detection method that detects an electric signal generated by an eyeball movement. The EOG detection method is accurate, but is difficult to implement on a daily basis because it requires a plurality of electrodes to be placed around the eye. In the case where self-counseling is conducted using eye data, for example, the eye data is preferably obtained in daily life without stress. Thus, low invasiveness and low contact are required in obtaining the eye data.

For example, the eye data can be obtained as an image by using an imaging device. Furthermore, recent advances in machine learning have enabled an eye area to be recognized and extracted from an obtained image. The eye includes a black area and a white area. The black area has an iris and a pupil that form a black part of the eye. The color of the iris is known to be genetically influenced.

The pupil has attracted attention among eye data because it is probably related to person's emotions, physical fatigue, or the like. However, the color of the iris might affect detection of the pupil condition. For example, the pupil and the iris are difficult to distinguish when the lightness of color of the iris is close to that of the pupil. An imaging device capable of taking an image using an infrared ray can provide an image that allows the iris and the pupil to be easily distinguished. The use of a strong infrared ray, however, might adversely affect the cornea, iris, lens, retina, and the like of the eye. The pupil also responds to the brightness of the environment or the like. Therefore, although the pupil has a correlation with person's conditions such as emotions and physical fatigue, a lot of environment-dependent noise is included.

When eye data is obtained, the eye blinks irregularly (hereinafter referred to as eye blinking). An example of eye blinking is blink reflex, which is a natural response to protect the eyeball from drying and the like. There are various types of eye blinking other than blink reflex. Thus, eye blinking might be included in eye data as noise components. Furthermore, in analysis using eye data, an image of a subject eye might be influenced by an irregular interval of eye blinking, the brightness of an ambient environment, and the like.

In view of the above problems, an object of one embodiment of the present invention is to provide a method for classifying person's conditions according to his/her eye data using a computer device. Another object of one embodiment of the present invention is to provide a method for generating learning data for learning eye data. Another object of one embodiment of the present invention is to provide a method for extracting an eye area from a group of images continuously captured by an imaging device, and extracting a feature amount from eye data. Another object of one embodiment of the present invention is to provide a method for training a classifier by supplying the classifier with the feature amount as learning data.

Note that the description of these objects does not preclude the existence of other objects. One embodiment of the present invention does not have to achieve all these objects. Other objects will be apparent from and can be derived from the description of the specification, the drawings, the claims, and the like.

Means for Solving the Problems

One embodiment of the present invention is a classification method using an imaging device, a feature extraction unit, and a classifier. Note that the classifier includes a classification model. The imaging device has a function of generating a group of images by continuous image capturing. The group of images includes an image of an eye area. The eye includes a black area and a white area. The black area includes an area formed with an iris and a pupil, and the white area is an area in which an eyeball is covered with a white coating. The classification method includes the steps in which the feature extraction unit extracts the eye area from the group of images, extracts a blinking amplitude from the group of images, detects an image for determining start of eye blinking from the group of images, stores an image for determining end of eye blinking from the group of images as first data, and stores an image after a predetermined time elapsed from the first data from the group of images as second data. The classification method includes the step in which the feature extraction unit extracts area data of the white area from the first data and the second data. The classification method includes the step in which the feature extraction unit supplies the area data of the white area to the classifier as learning data. The classification method includes the step in which the classifier generates a classification model using the learning data.

In the above structure, the images of the eye areas included in the first data and the second data each include the black area and the white area. In the case where the detected area data of the white area includes a first area and a second area independently, the classification method includes the step in which the feature extraction unit outputs the ratio between the first area and the second area. In the case where the detected area data of the white area is detected as a third area, the classification method includes the steps in which the feature extraction unit detects a circle area from the third area, obtains the center of the circle from the circle area, divides the third area into the first area and the second area using the x-coordinate of the center of the circle, and outputs the ratio between the first area and the second area. The classification method includes the step in which the feature extraction unit calculates an oscillation width of a white part of the eye from the ratio between the first area and the second area. The classifier preferably uses the oscillation width of the white part of the eye as the learning data.

In each of the above structures, the classification method includes the step in which the feature extraction unit supplies the oscillation width of the white part of the eye and the blinking amplitude as the learning data to the classifier. The classification method preferably includes the step in which the classifier generates the classification model using the oscillation width of the white part of the eye and the blinking amplitude.

In each of the above structures, the classification method includes the step of training the classifier using the learning data. The classification method includes the step of supplying new first data and new second data to the feature extraction unit. The classification method preferably includes the step in which the classifier classifies person's emotional or physical conditions using the classification model.

In each of the above structures, the classification method includes the step of attaching a teacher label to the learning data. The classification method preferably includes the step of training the classifier using the learning data to which the teacher label is attached.

Effect of the Invention

One embodiment of the present invention can provide a method for classifying person's conditions according to his/her eye data using a computer device. Another embodiment of the present invention can provide a method for generating learning data for learning eye data. Another embodiment of the present invention can provide a method for extracting an eye area from a group of images continuously captured by an imaging device, and extracting a feature amount from eye data. Another embodiment of the present invention can provide a method for generating a classifier by supplying the classifier with the feature amount as learning data.

Note that the effects of one embodiment of the present invention are not limited to the effects listed above. The effects listed above do not preclude the existence of other effects. Note that the other effects are effects that are not described in this section and will be described below. The effects that are not described in this section are derived from the description of the specification, the drawings, or the like and can be extracted from the description by those skilled in the art. Note that one embodiment of the present invention is to have at least one of the effects listed above and/or the other effects. Accordingly, depending on the case, one embodiment of the present invention does not have the effects listed above in some cases.

MODE FOR CARRYING OUT THE INVENTION

Embodiments are described in detail with reference to the drawings. Note that the present invention is not limited to the following description, and it will be readily appreciated by those skilled in the art that modes and details of the present invention can be modified in various ways without departing from the spirit and scope of the present invention. Therefore, the present invention should not be interpreted as being limited to the description of the embodiments below.

Note that in structures of the invention described below, the same portions or portions having similar functions are denoted by the same reference numerals in different drawings, and a description thereof is not repeated. Furthermore, the same hatch pattern is used for the portions having similar functions, and the portions are not especially denoted by reference numerals in some cases.

In addition, the position, size, range, or the like of each structure shown in drawings does not represent the actual position, size, range, or the like in some cases for easy understanding. Therefore, the disclosed invention is not necessarily limited to the position, size, range, or the like disclosed in the drawings.

(Embodiment)

In this embodiment, a method for classifying person's conditions according to eye data will be described with reference to FIG. 1 to FIG. 9. Note that the description in this embodiment is made focusing on one of the left and right eyes. The structures and methods shown in this embodiment can be used for both of the left and right eyes.

The method for classifying person's conditions according to eye data described in this embodiment is controlled by a program that operates on a computer device. Thus, the computer device can be referred to as a classification device provided with the method for classifying person's conditions according to eye data. The classification device for classifying person's conditions according to eye data will be described in detail with reference to FIG. 9. The program is stored in a memory or a storage included in the computer device. Alternatively, the program is stored in a computer connected via a network (e.g., LAN (Local Area Network), WAN (Wide Area Network), or the Internet) or a server computer including a database.

The classification device provided with the method for classifying person's conditions according to eye data includes an imaging device, a feature extraction unit, and a classifier. The imaging device is capable of generating a group of images and storing the group of images in a memory or a storage included in a computer device. The group of images means continuously captured images, moving images, and the like, i.e., a plurality of images. Thus, the classification device can use the group of images stored in the memory or the storage included in the computer device. For example, in the case where the classification device is incorporated in a portable terminal such as a mobile device, the classification device preferably includes an imaging device. The group of images may be supplied to the classification device from a camera connected to a network, such as a web camera (including a monitoring camera).

The group of images preferably includes the face of a subject person. From the images storing the person's face, an image of an eye area can be extracted using machine learning. For processing in the machine learning, artificial intelligence (AI) is preferably used. For example, an artificial neural network (ANN) can be specifically used for extracting an image of an eye area. Note that in one embodiment of the present invention, an artificial neural network is just referred to as a neural network (NN) in some cases. Arithmetic processing of the neural network is achieved with a circuit (hardware) or a program (software).

For example, in the case where an image of an eye area is retrieved from images storing a person's face, a typical image of the eye area can be supplied as a query image. An area with high similarity to the query image is extracted from the images storing person's face included in the group of images. In the case where the area with high similarity is retrieved, for example, a convolutional neural network (CNN), pattern matching, or the like can be used for the image retrieval method. Note that in one embodiment of the present invention, it is only necessary that a query image is registered, and a query image does not necessarily supplied every time when retrieval is performed. The extracted eye area is stored as an image.

Detailed eye data is extracted from the extracted image of the eye area. The eye includes a black area and a white area. The black area includes an area formed with an iris and a pupil, and the white area refers to an area in which an eyeball is covered with a white coating (sometimes referred to as a sclera). The maximum width of the area interposed between an upper eyelid and a lower eyelid is defined as a blinking amplitude. The minimum value of the area interposed between the eyelids is defined as a minimum value of the blinking amplitude. Note that the group of images stores various eye conditions. The blinking amplitude can be obtained by selecting the top plurality of blinking amplitudes from the detected ones and calculating the average value.

Here, the function of the feature extraction unit is described. The feature extraction unit has a function of extracting detailed eye data from the extracted image of the eye area. The feature extraction unit performs the following processing on each image storing a person's face included in the group of images. The following processing is a method of creating learning data of the eye with reduced influence of noise due to eye blinking.

The above method includes the step of extracting an image of an eye area from images storing a person's face.

The above method also includes the step of extracting a blinking amplitude from the image of the eye area by the feature extraction unit. The feature extraction unit extracts the blinking amplitude, thereby setting a determination threshold value for detecting eye blinking in subsequent steps. The half width of the blinking amplitude can be set as the determination threshold value, for example. Note that the determination threshold value is preferably a different value that can be set for each subject person. When the group of images is converted into a group of images of the eye area, the images processed by the computer can be reduced in size. This can reduce the usage amount of the memory and lead to lower power consumption.

The above method also includes the step of detecting an image for determining the start of eye blinking from the images of the eye area by the feature extraction unit. Note that the start of eye blinking means the detection of an image from which it can be determined that the eyelids are closed. The end of eye blinking means the detection of an image from which it can be determined that the eyelids are opened. Whether the eyelids are closed or opened can be determined using the determination threshold value.

Eye blinking is determined from the blinking amplitude extracted from an image of the start of eye blinking, the blinking amplitude extracted from an image of the end of eye blinking, and an image from which an amplitude smaller than the blinking amplitudes extracted at the start and end of eye blinking is extracted. A blinking time is said to be approximately 300 ms, although it varies from person to person. In the imaging device, at least three or more images of eye areas with smaller blinking amplitudes than the determination threshold value are preferably obtained in the blinking time.

The above method also includes the step of storing as first data an image after a predetermined time elapsed from the image for determining the end of eye blinking from the images of the eye area by the feature extraction unit. The first data represents an eye condition after eye blinking. Thus, the first data represents person's conditions almost properly in the case where eye blinking occurs due to blink reflex. Note that the predetermined time is preferably set freely.

The above method also includes the step of storing as second data an image after a predetermined time elapsed from the first data by the feature extraction unit. The second data generally represents person's emotional or physical conditions. Note that the predetermined time is preferably set freely.

For example, in the case where a person feels an intense emotion, his/her eyes stored in the second data are larger or smaller than the eyes stored in the first data. For another example, in the case where a person feels sleepy, the amplitude of his/her eyes stored in the second data is smaller than that of the eyes stored in the first data. Note that an eye blinking rate can also be used for determination of sleepiness or the like. The eye blinking rate means the number of times of eye blinking per minute.

The above method also includes the step of extracting area data of the white area from the first data and the second data by the feature extraction unit. In one embodiment of the present invention, the data obtained from the white area can be used to determine the state of eyeball movement. The area data of the white area is, for example, an area ratio when the white area is divided into a first area and a second area using the center coordinates of the black part of the eye, or a change in the areas of the first area and the second area that change with the opening and closing of the eyelids.

For example, it is known that the black part of the eye is in constant motion even when the gaze stays in the same place. This is called a fixational eye movement, and the largest single fixational eye movement is called a microsaccade. The microsaccade serves to prevent light entering from the pupil from keeping hitting the same spot on the retina. In the case where no microsaccade occurs and light entering from the pupil keeps hitting the same spot on the retina, the retina cannot recognize a change in light. It is thus known that the retina cannot recognize an image entering through the pupil. In one embodiment of the present invention, the oscillation width of the black part of the eye generated by a microsaccade can be detected from the area ratio of the white part of the eye to detect the microsaccade. Note that in the description, the oscillation width of the black part of the eye generated by the microsaccade is sometimes referred to as the oscillation width of the white part of the eye. Note that the oscillation width of the black part of the eye and the white part of the eye can also be referred to the oscillation width of the eyeball.

It is said that the eye is in a state of high capability to produce vision when the movement of the microsaccade is large and fast. In other words, when the movement of the microsaccade is large and fast, the person is in a condition of high concentration on the object. When the movement of the microsaccade is small and slow, the person can be regarded as being in a condition of losing concentration on the object. In this state, it can be determined that the person feels sleepy. Note that in order to classify the person's conditions more accurately, determination is preferably performed using a plurality of conditions such as the area ratio of the white part of the eye, the blinking amplitude, and the oscillation width of the white part of the eye.

The above method also includes the step of supplying data on the white area as learning data to the classifier by the feature extraction unit. As the learning data, for example, the data on the white area such as the area ratio of the white part of the eye, the blinking amplitude, the oscillation width of the white part of the eye, and a change in the position of the eyelids is preferably supplied.

The above method also includes the step of generating a classification model using the learning data by the classifier.

Unsupervised machine learning classification can be performed using the above learning data. For example, an algorithm such as K-means or DBSCAN (density-based spatial clustering of applications with noise) can be used for the classification model.

As another example, teacher data can be further supplied to the classification model. For example, emotion classification or the determination threshold value of the oscillation width of the white part of the eye can be supplied as the teacher data. Classification by supervised machine learning can be performed using learning data to which the teacher data is supplied. For the classification model, a machine learning algorithm such as a decision tree, Naive Bayes, KNN (k Nearest Neighbor), SVM (Support Vector Machines), perceptron, logistic regression, or a neural network can be used.

Figure 1:
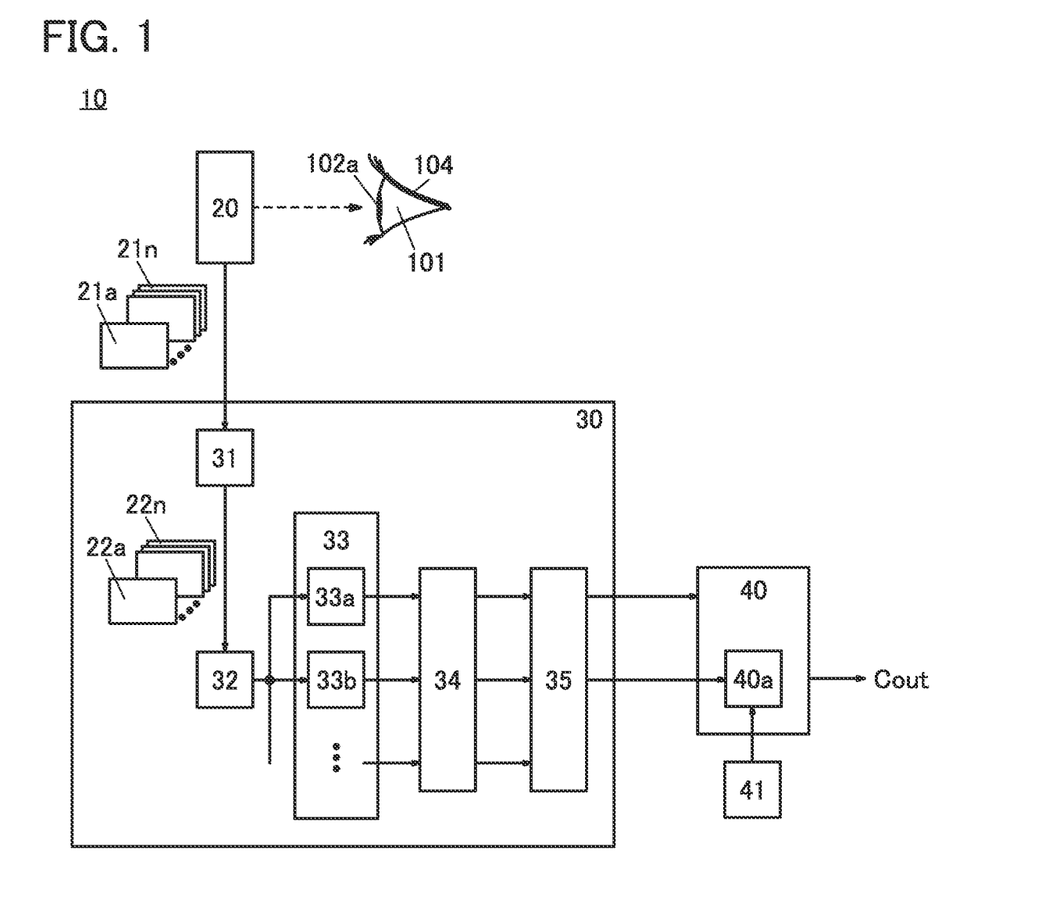
FIG. 1 is a block diagram illustrating a method for classifying person's conditions according to eye data.

Next, a method for classifying person's conditions according to the eye data described in this embodiment will be described with reference to FIG. 1. In the following description, the generation method of the classifier is referred to as a classification device 10 in some cases.

The classification device 10 includes an imaging device 20, a feature extraction unit 30, and a feature estimation unit 40. The feature extraction unit 30 includes an eye blinking detection unit 31, a memory control unit 32, a storage unit 33, a detection unit 34, and a data detection unit 35. The feature estimation unit 40 includes a classifier 40a. The storage unit 33 includes a storage device 33a and a storage device 33b. Note that the number of storage devices included in the storage unit 33 is not limited to two, and may be one or three or more.

The imaging device 20 can capture an image 21a to an image 21n of a person with use of a capture element included in the imaging device 20. The images include a person's eye area. The eye area includes a white area 101, a black area 102a, and eyelids 104. The black area includes a pupil area and an iris area. The image 21a to the image 21n are supplied to the eye blinking detection unit 31. Note that a or n is a positive integer. Furthermore, n is larger than a.

The eye blinking detection unit 31 can extract the eye area from each of the image 21a to the image 21n. The eye blinking detection unit 31 stores the extracted eye areas as an image 22a to an image 22n. Note that each of the image 22a to the image 22n is preferably converted into an image with the same pixel number, and is also preferably converted into an image with the same width of the eye. In the case where any one image of the image 22a to the image 22n is described below, the image is sometimes referred to as an image 22 of an eye area for simplicity. Note that the eye blinking detection unit 31 preferably uses a CNN to extract the eye area.

The eye blinking detection unit 31 can extract a blinking amplitude from the images of the eye area. The blinking amplitude is preferably the maximum value of the distance between the upper eyelid and the lower eyelid in a state where the eyes are determined to be opened, or the average value of the maximum values of the distances extracted from a plurality of images. The eye blinking detection unit 31 can determine a determination threshold value for determining whether the image of the eye area is in the state of eye blinking with use of the blinking amplitude.

With use of the determination threshold value, the eye blinking detection unit 31 can detect an image 22p for determining the start of eye blinking from the image 22a to the image 22n. For example, the eye blinking detection unit 31 can determine the start of eye blinking when detecting the time at which the blinking amplitude extracted from the image 22p is smaller than the determination threshold value. Then, the eye blinking detection unit 31 detects an image for determining the end of eye blinking from images after the image 22p. For example, the eye blinking detection unit 31 can determine the end of eye blinking when detecting the time at which the blinking amplitude extracted from an image after the image 22p is larger than the determination threshold value. Note that p is a positive integer.

In the case where an image $22p_{+2}$ is an image for determining the end of eye blinking, for example, an image $22p_{+3}$ can be supplied to the memory control unit 32 as the first data. The memory control unit 32 stores the image $22p_{+3}$ in the storage device 33a. Note that in one embodiment of the present invention, the image $22p_{+3}$, which is the next image of the image $22p_{+2}$ for determining the end of eye blinking, is stored in the storage device 33a as the first data, but the image stored as the first data is not limited to the next image of the image $22p_{+2}$. An image $22q$ after a predetermined time elapsed can also be stored. Note that q is a positive integer. Furthermore, q is larger than p.

The eye blinking detection unit 31 can supply an image $22r$ after a predetermined time elapsed from the image $22p_{+3}$ to the memory control unit 32 as the second data. The memory control unit 32 stores the image $22r$ in the storage device 33b. Note that r is a positive integer. Furthermore, r is larger than q.

The number of storage devices is not limited to two. Images of eye areas after different times elapsed from one time of eye blinking can be stored in a plurality of storage devices. Note that processing in the eye blinking detection unit 31 will be described in detail with reference to FIG. 3 and FIG. 4.

The detection unit 34 can extract the area data of the white area from the first data stored in the storage device 33a and the second data stored in the storage device 33b. The use of a CNN is efficient to extract the area data of the white area.

Figure 6A:
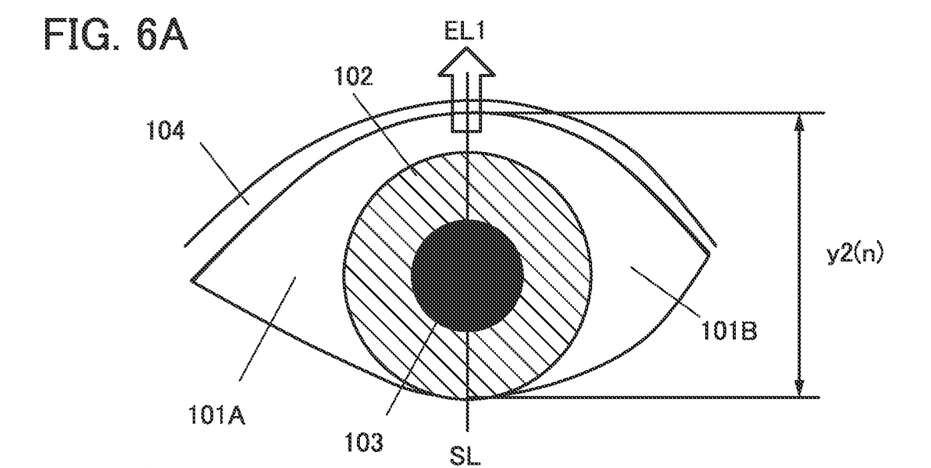
FIG. 6A is a diagram illustrating eye data.
Figure 6B:
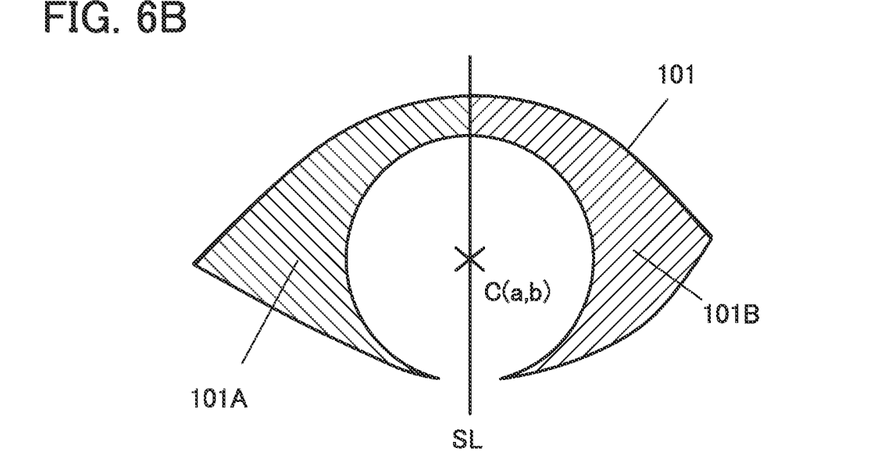
FIG. 6B and FIG. 6C are diagrams illustrating extracted white areas.
Figure 6C:
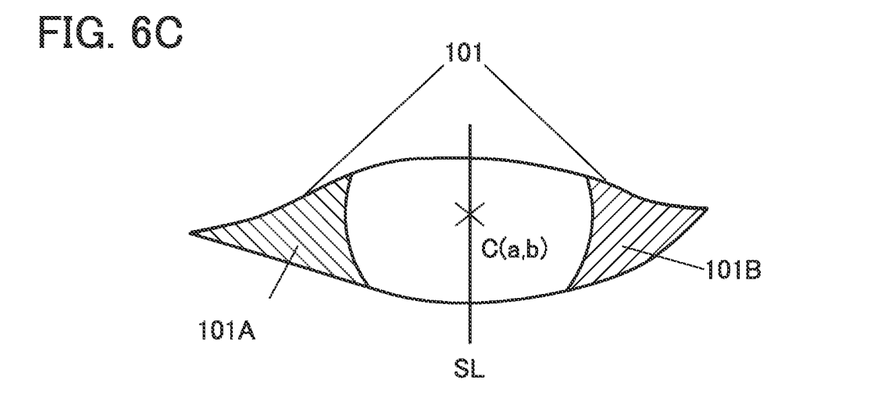

The data detection unit 35 can detect more detailed data of the white area from the area data of the white area extracted by the detection unit 34. For example, the white area can be divided into a first area and a second area using the center coordinates of the black part of the eye. The area ratio between the first area and the second area can also be extracted. It is also possible to extract a change in the areas of the first area and the second area that is caused by opening and closing of the eyelids. The method for extracting the area data of the white area will be described in detail with reference to FIG. 6. Note that the detection unit 34 and the data detection unit 35 can extract the size of the pupil from the black area.

The data of the white area extracted by the feature extraction unit 30 is supplied to the feature estimation unit 40 as learning data. As the learning data, for example, the area ratio of the white part of the eye, the blinking amplitude, the oscillation width of the white part of the eye, and a change in the position of the eyelids are supplied to the classifier 40a. Moreover, the size of the pupil, and the like may also be supplied.

The classifier 40a included in the feature estimation unit 40 can generate the classification model using the learning data. Teacher data 41 can also be supplied to the classification model. As the teacher data 41, for example, emotion classification or the determination threshold value of the oscillation width of the white part of the eye can be supplied. Supplying the learning data and the teacher data trains the classification model. Accordingly, the classifier 40a including the classification model can estimate person's emotional or physical conditions from the eye data.

Then, new first data and new second data are supplied to the feature extraction unit 30. New learning data is supplied to the feature estimation unit 40. The feature estimation unit 40 can classify person's emotional or physical conditions using the classifier 40a including the classification model that has been trained, thereby outputting a classification result Cout.

Figure 2A:
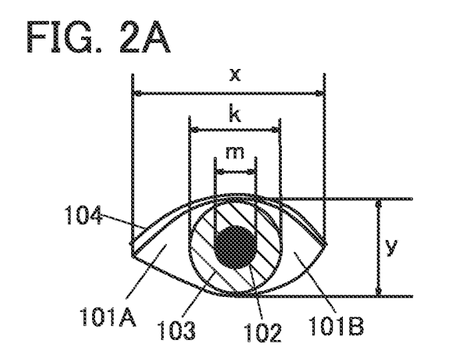
FIG. 2A is a diagram illustrating a structure of an eye.

FIG. 2A is a diagram illustrating a structure of an eye. Components of the eye include a white area, a black area, the eyelids 104, and the like. The white area includes a white area 101A and a white area 101B, which are separated by the black part of the eye. The black area includes a pupil 102 and an iris 103. Next, the size of each component of the eye is defined. For example, the eye can be defined as follows: the width in the lateral direction of the eye is x; the width of the iris is k; the width of the pupil is m; and the width in the vertical direction of the eye (blinking amplitude is y).

Figure 2B:
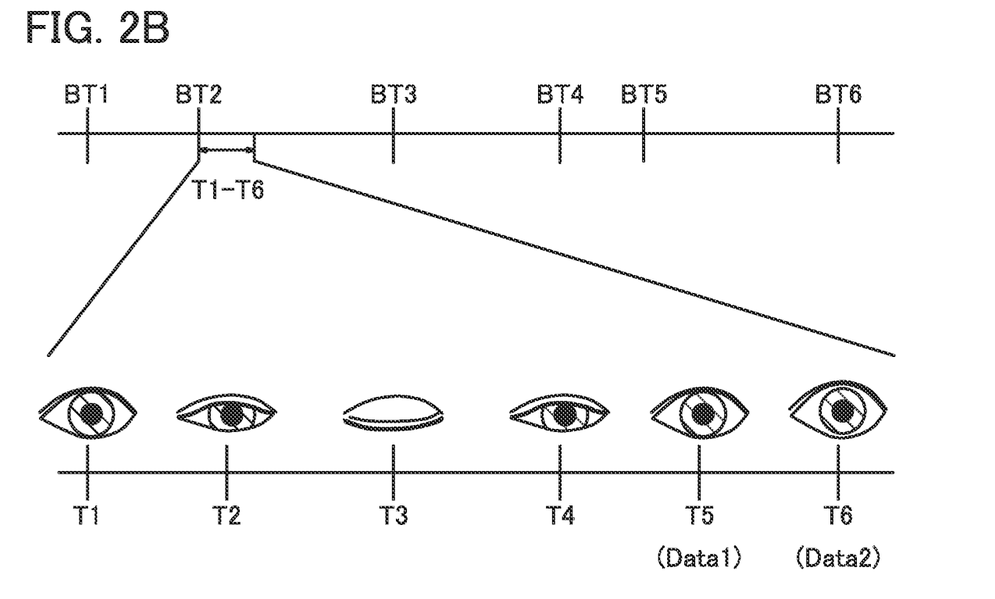
FIG. 2B is a diagram illustrating a method for generating learning data.

FIG. 2B is a diagram illustrating a method for generating learning data. Eye blinking irregularly occurs in the eye. As an example, Time BT1 to Time BT6 are shown as the times at which eye blinking occurs in FIG. 2B. It is important to stably acquire eye data in order to generate learning data for the eye. For example, an image of eye blinking needs to be removed as noise from the image 22a to the image 22n. In the case where a group of images including an image of eye blinking is used as learning data, a classification model needs to learn a larger number of images. With a larger number of images to be learned, the classification device 10 consumes larger power and takes a longer time to process the images.

In one embodiment of the present invention, eye blinking is used as a trigger for the occurrence of an event. As an example, eye blinking at Time BT2 is described in detail.

Time T1 is a state before the start of eye blinking (a state in which an event has not occurred).

At Time T2, it is determined that the blinking amplitude y becomes smaller than the determination threshold value. More specifically, the eye blinking detection unit 31 detects the image $22p$ for determining the start of eye blinking.

At Time T3, it is determined that the blinking amplitude y is smaller than the determination threshold value and smaller than the blinking amplitude y detected in the image $22p$. More specifically, the eye blinking detection unit 31 detects an image $22p_{+1}$ for determining that the blinking amplitude y is the smallest.

At Time T4, it is determined that the blinking amplitude y becomes larger than the determination threshold value. More specifically, the eye blinking detection unit 31 detects the image $22p_{+2}$ for determining the end of eye blinking.

At Time T5, the image $22p_{+3}$ after the end of eye blinking is detected. Note that the image $22p_{+3}$ is stored in the storage device 33a as Data 1. The image $22q$ after a predetermined time elapsed from Time T4 may be Data 1.

Time T6 is the image $22r$ after a predetermined time elapsed from the time at which image $22p_{+3}$ was detected. Note that the image $22r$ is stored in the storage device 33b as Data 2.

The aforementioned process of Time T1 to Time T6 makes it possible to generate the learning data having a reduced amount of noise, reduced power consumption, and a reduced number of storage devices needed.

Data 1 and Data 2 can each be handled as independent learning data. Alternatively, Data 1 and Data 2 can be handled as single learning data. Alternatively, a difference in data is extracted from Data 2 to generate third data, and the third data can be used as the learning data. Note that Data 1, Data 2, and the third data can be used as leaning data for another machine learning. The occurrence frequency of eye blinking or the width of the pupil can be added to Data 1, Data 2, and the third data. The occurrence frequency of eye blinking or the width of the pupil can also be used as a piece of learning data representing person's emotional or physical conditions.

Figure 3:
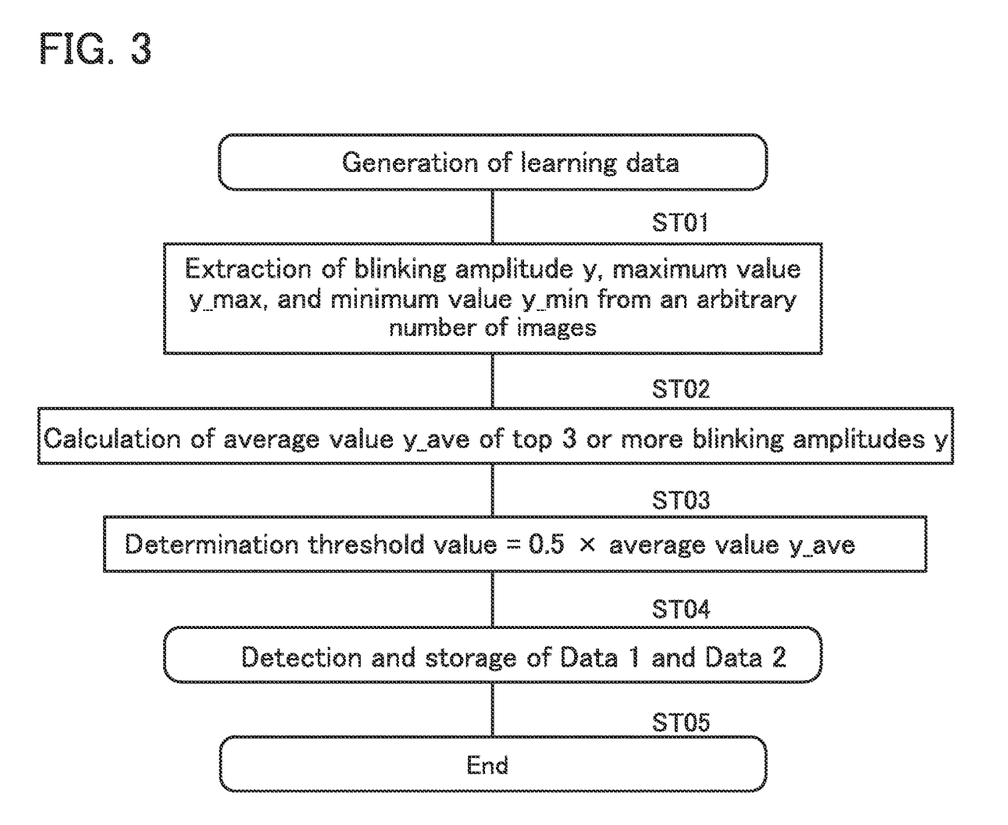
FIG. 3 is a flowchart illustrating a method for generating learning data.

FIG. 3 is a flowchart illustrating a method for generating learning data. First, a blinking amplitude is extracted using the group of images, the image 22a to the image 22n. Then, a determination threshold value for determining the start and end of eye blinking is set using the blinking amplitude.

In Step ST01, the blinking amplitude y is extracted from an arbitrary number of images in the group of images. Note that in Step ST01, a maximum value y_max of the blinking amplitude y and a minimum value y_min of the blinking amplitude y are also extracted. The minimum value y_min of the blinking amplitude y denotes the minimum value extracted from the images. When the maximum value y_max of the blinking amplitude y and the minimum value y_min of the blinking amplitude y are constantly subjected to additive-averaging, features such as the degree of eye opening of a subject person can be extracted.

In Step ST02, the average value of the blinking amplitude y is calculated. As an example, an average value y_ave is calculated using the top three or more blinking amplitudes y extracted in Step ST01. Note that the number of blinking amplitudes to be averaged is preferably set.

In Step ST03, a determination threshold value for determining the start and end of eye blinking is set. As an example, 50% of the average value y_ave is set as the determination threshold value in the case where the start and end of eye blinking are used as determination conditions. Note that the determination conditions of the start and end of eye blinking are not limited to 50% and are each preferably set as appropriate.

In Step ST04, Data 1 and Data 2 are detected and stored. Note that detection and storage of Data 1 and Data 2 will be described in detail with reference to FIG. 4.

In Step ST05, generation of the learning data is ended.

Figure 4:
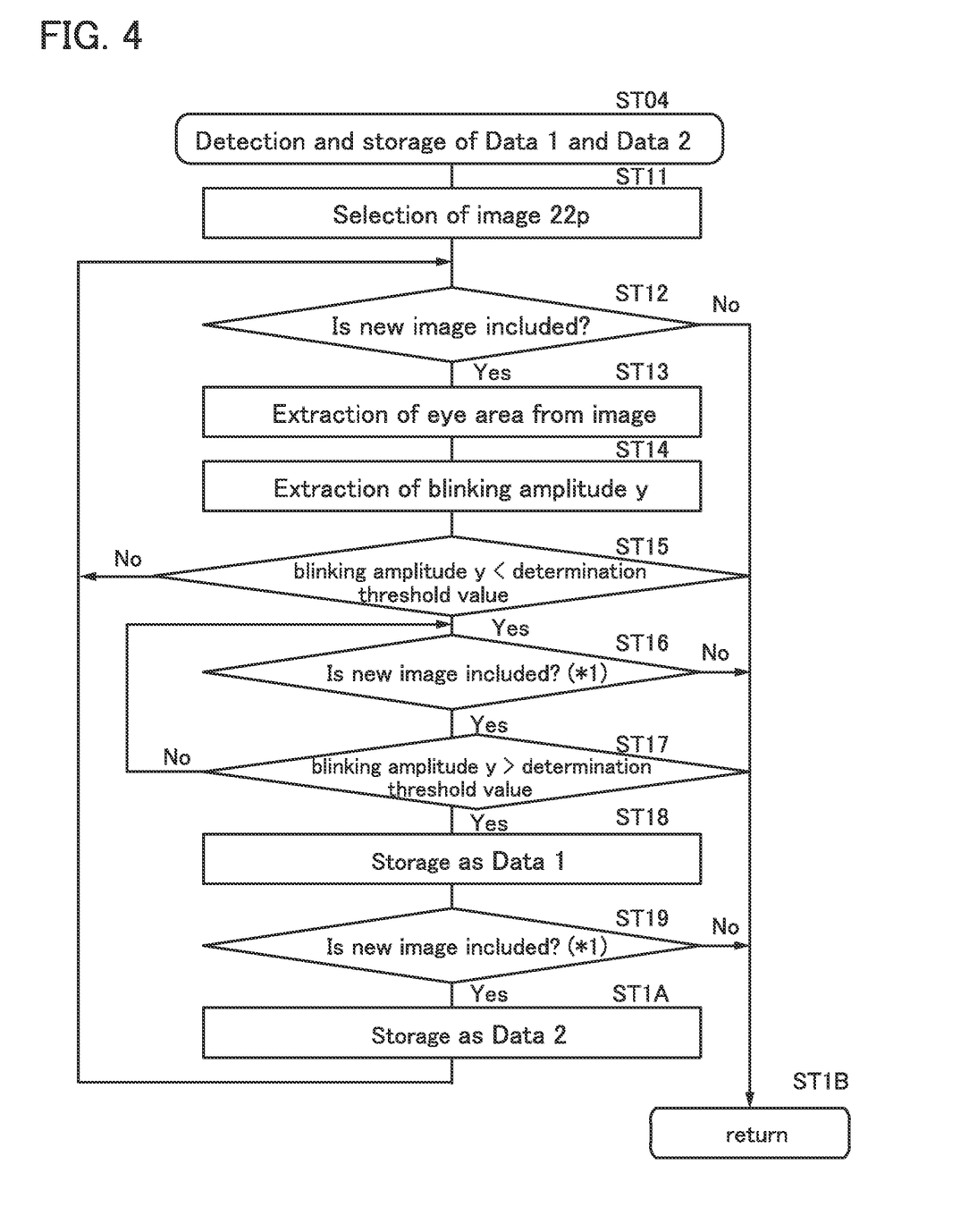
FIG. 4 is a flowchart illustrating a method for generating learning data.

FIG. 4 is a flowchart illustrating a method for generating learning data. In FIG. 4, a method for detecting and storing Data 1 and Data 2 as the learning data is described in detail. Note that in FIG. 4, the group of images, the image 22a to the image 22n, in which eye areas are stored as images is used.

In Step ST11, an arbitrary image 22p is selected from the group of images.

In Step ST12, whether a new image is included is checked. If the image $22p_{+1}$ is present, the process proceeds to Step ST13. If the image $22p_{+1}$ is not present, the process proceeds to Step ST1B (return) and then proceeds to Step ST05, so that the generation of the learning data is ended.

In Step ST13, an eye area is extracted from the image.

In Step ST14, the blinking amplitude y is extracted from the eye area.

In Step ST15, whether the blinking amplitude y is smaller than the determination threshold value is determined. When the blinking amplitude y is smaller than the determination threshold value, it is determined that eye blinking has started and the process proceeds to Step ST16. When the blinking amplitude y is larger than the determination threshold value, it is determined that eye blinking has not started and the process proceeds to Step ST12.

In Step ST16, whether a new image is included is checked. If the image $22p_{+2}$ is present, the process proceeds to Step ST17. If the image $22p_{+2}$ is not present, the process proceeds to Step 1B and then proceeds to Step ST05, so that the generation of the learning data is ended. Note that Step ST16 includes the processing of Step ST13 and Step ST14, which is represented by a symbol "*1" due to the space limitation of the drawing. The step with the symbol "*1" thereafter includes the processing of Step ST13 and Step ST14.

In Step ST17, whether the blinking amplitude y is larger than the determination threshold value is determined. When the blinking amplitude y is larger than the determination threshold value, it is determined that eye blinking has ended and the process proceeds to Step ST18. When the blinking amplitude y is smaller than the determination threshold value, it is determined that eye blinking has not ended and the process proceeds to Step ST16.

In Step ST18, the image $22p_{+3}$ is stored in the storage device 33a as Data 1.

In Step ST19, whether a new image is included is checked. If the image 22r is present, the process proceeds to Step ST1A. If the image 22r is not present, the process proceeds to Step ST1B and then proceeds to Step ST05, so that the generation of the learning data is ended.

In Step ST1A, the image 22r is stored in the storage device 33b as Data 2. Next, the process proceeds to Step ST12.

As described above, eye blinking is detected as an event and images after a predetermined time elapsed from the end of eye blinking can be collected as learning data. Since the learning data is collected under the condition that it is after eye blinking, noise components can be reduced in the learning data. Data on the number of times of eye blinking and the like can be easily collected when a counter or the like is provided in Step ST16 or the like.

Figure 5A:
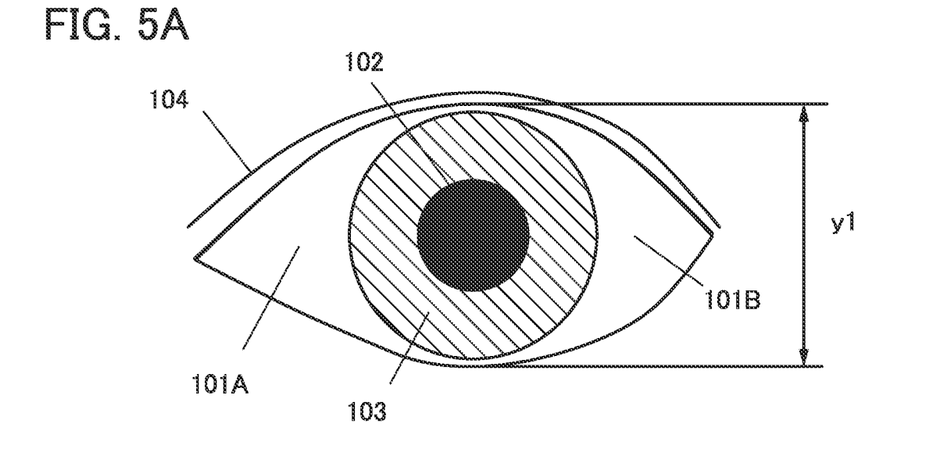
FIG. 5A to FIG. 5C are diagrams illustrating eye data.
Figure 5B:
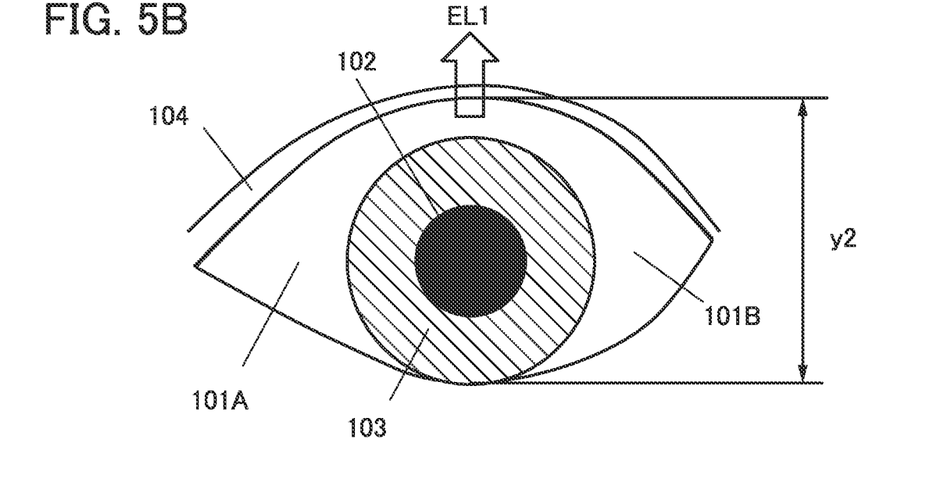
Figure 5C:
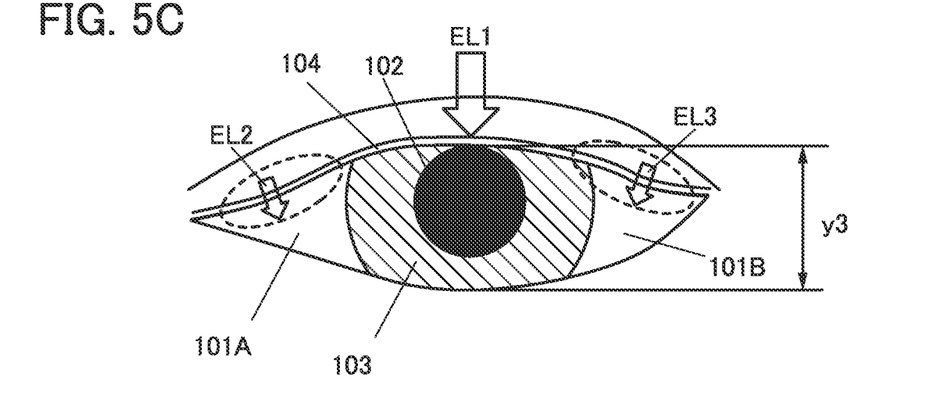

FIG. 5A to FIG. 5C are diagrams illustrating eye data. FIG. 5A shows an eye condition after eye blinking as an example. That is, FIG. 5A corresponds to Data 1. The eye after eye blinking usually represents emotional or physical conditions of a person in the image that he or she is not aware of Note that a blinking amplitude y1 in FIG. 5A is preferably greater than −20% and less than +20 of the average value y_ave. Further preferably, the blinking amplitude y1 is greater than −10% and less than +10% of the average value y_ave. Still further preferably, the blinking amplitude y1 is greater than −5% and less than +5% of the average value y_ave.

The detection unit 34 and the data detection unit 35 can calculate as eye data the area of the white area 101A, the area of the white area 101B, the total area of the white area 101A and the white area 101B, the area ratio between the white area 101A and the area 101B, and the like. The detection unit 34 and the data detection unit 35 preferably use a CNN to extract each area.

FIG. 5B shows an eye condition after a predetermined time elapsed from eye blinking as an example. After a predetermined time elapsed from eye blinking, facial muscles of the eye might be affected by the person's emotional or physical conditions. If the facial muscles are affected, a change in the blinking amplitude y2, the pupil, or the like appears. FIG. 5B shows, as an example, a change in the eye shape that appears when a person is surprised or feels an intense emotion. For example, the upper eyelid 104 moves upward as indicated by a direction EL1. This change can be detected as a change in the total area of the white area 101A and the area 101B.

As another example, FIG. 5C shows an eye condition after a predetermined time elapsed from eye blinking, which is different from that in FIG. 5B. The eye condition after a predetermined time elapsed from eye blinking usually represents person's emotional or physical conditions that appear in the period from one time of eye blinking to the next time of eye blinking. FIG. 5C shows, as an example, a change in the eye shape that appears when a person feels sleepy. If the facial muscles are affected, a change in a blinking amplitude y3, the pupil, or the like appears. For example, the upper eyelid 104 moves downward as indicated by the direction EL1. Note that the blinking amplitude y3 is preferably larger than the determination threshold value.

This change can be detected as a change in the areas of the white area 101A and the area 101B. As shown in FIG. 5C, the amount of change in a direction EL2 is different from that in a direction EL3 in some cases. Such a slight change might respond to person's emotions, which is effective in self-counseling.

Thus, FIG. 5B and FIG. 5C correspond to Data 2 in many cases. Note that FIG. 5B or FIG. 5C sometimes shows an eye condition after eye blinking; if the condition of a person after eye blinking is as shown in FIG. 5B or FIG. 5C, it possibly represents person's emotional or physical conditions clearly. Note that these classifications are performed using a classification model that has been trained using learning data.

As another example, a person having the eye condition shown in FIG. 5C is sometimes in a condition of high concentration. In order to distinguish such a case, a method utilizing the oscillation width of a microsaccade can be used.

In one embodiment of the present invention, the oscillation width of the white part of the eye (eyeball) generated by a microsaccade can be detected from the area ratio of the white part of the eye. A method for detecting the oscillation width of the white part of the eye will be described in detail with reference to FIG. 6.

FIG. 5B is referred to for the description of the method for detecting the oscillation width of the white part of the eye in FIG. 6A. In order to detect the oscillation width of the white part of the eye, the area of the white part of the eye needs to be obtained. In the case where the white area is detected as an object as shown in FIG. 6A, a dividing line SL for dividing the white area needs to be set.

FIG. 6B is a diagram illustrating the white area of FIG. 5B, which is extracted by the detection unit 34. Note that the white area 101 is extracted as an object. In the case where a single object is extracted, the data detection unit 35 extracts a circle area approximately equal to the black area from the white area. Next, center coordinates C(a, b) of the extracted circle are detected. Then, the x-coordinate of the center coordinates can be used to set the dividing line SL for dividing the white area 101 into the white area 101A and the white area 101B.

FIG. 6C is a diagram illustrating the white area of FIG. 5C, which is extracted by the detection unit 34. Note that the white area 101 is extracted as two objects showing the white area 101A and the white area 101B.

In FIG. 6B and FIG. 6C, the white area 101A and the white area 101B are separated by the dividing line SL. For example, in order to detect the oscillation width of the black part of the eye, a change in the center of the black part of the eye is preferably detected. Note that the detection accuracy of the oscillation width of the black part of the eye depends on the definition capacity of the number of pixels in the image. In contrast, the amount of change in the oscillation width of the target white part of the eye can be compared in area and the white area 101A and the white area 101B are inversely proportional, i.e., one of them definitely decreases when the other increases. Thus, the accuracy of detecting the oscillation width of the white part of the eye is higher than that of the black part of the eye.

Figure 7:
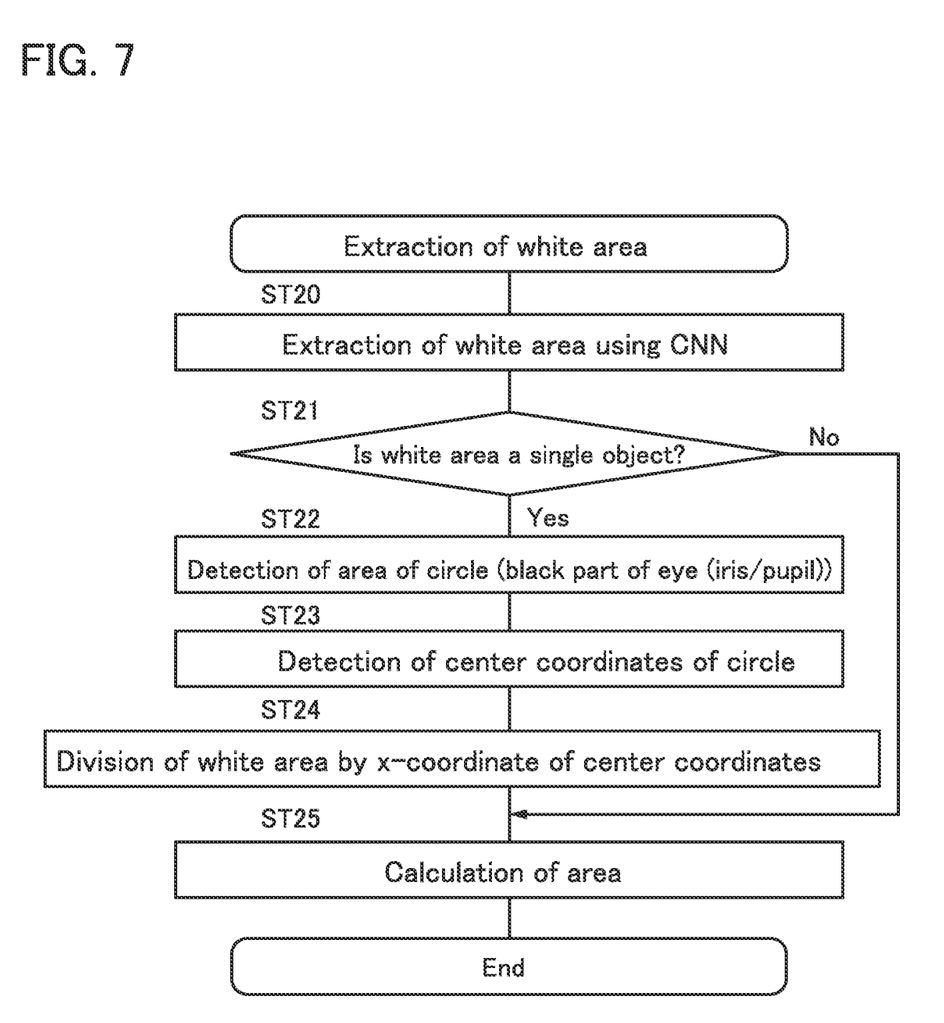
FIG. 7 is a flowchart illustrating a method for detecting a white area.

FIG. 7 is a flowchart illustrating a method for detecting the white area.

In Step ST20, a white area is extracted from an image of an eye area with use of a CNN.

In Step ST21, whether the white area is a single object is determined. In the case where the white area is detected as a single object, the process proceeds to Step ST22. In the case where the white area is detected as a plurality of objects, the process proceeds to Step ST25.

In Step ST22, an area of a circle (black part of eye (iris and pupil)) is detected from the white area detected as a single object.

In Step ST23, center coordinates C(a, b) of the circle area are detected.

In Step ST24, the white is divided by the x-coordinate of the center coordinates C(a, b). The white area 101 is divided into the white area 101A and the white area 101B.

In Step ST25, the area of the detected white area 101A and the area of the detected white area 101B are each calculated.

Figure 8A:
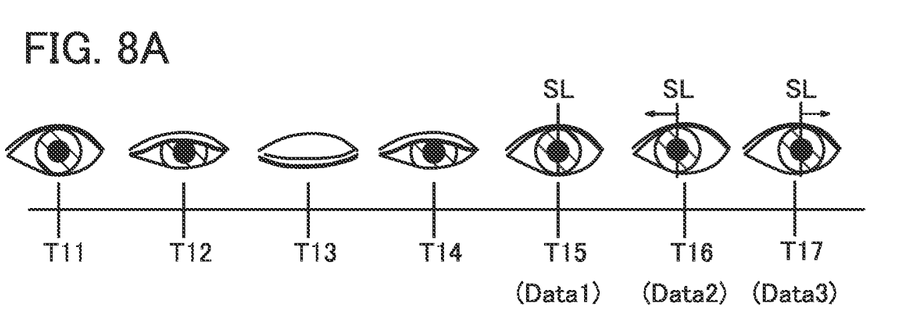
FIG. 8A to FIG. 8C are diagrams illustrating a method for generating learning data.
Figure 8B:
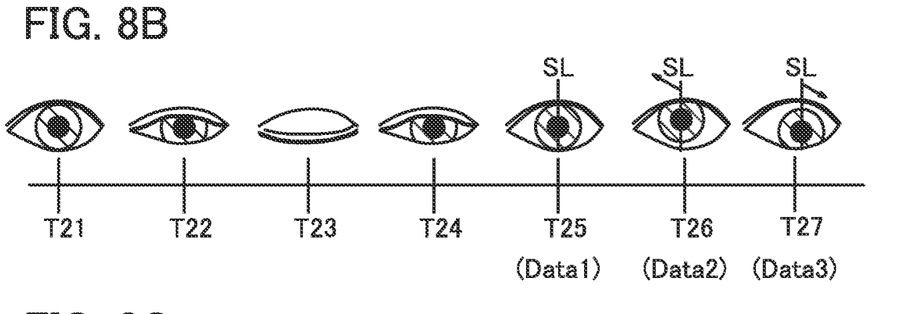
Figure 8C:
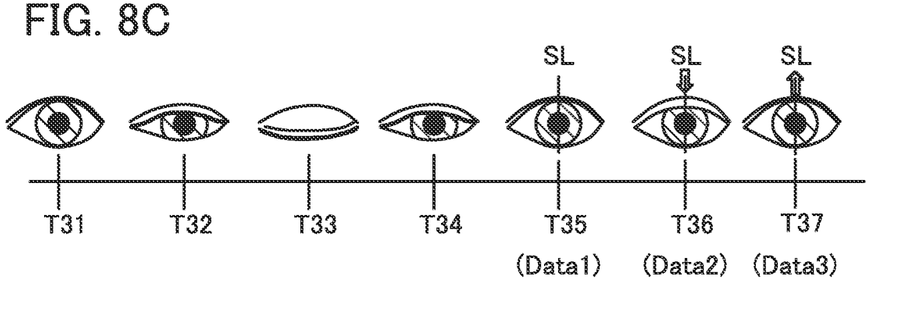

FIG. 8A to FIG. 8C are diagrams illustrating a method for generating learning data. In FIG. 8A to FIG. 8C, Time T11, Time T21, and Time T31 are times before eye blinking starts. At Time T12, Time T22, and Time T32, the feature extraction unit 30 detects the start of eye blinking. At Time T13, Time T23, and Time T33, the eye blinking detection unit 31 detects an image for determining that the blinking amplitude y is the smallest. At Time T14, Time T24, and Time T34, the feature extraction unit 30 detects the end of eye blinking. Time T15, Time T25, and Time T35 are times after a predetermined time elapsed from the end of eye blinking. Time T16, Time T26, and Time T36 are times after a predetermined time further elapsed from the end of eye blinking. Time T17, Time T27, and Time T37 are times after a predetermined time further elapsed from the end of eye blinking, which are different from Time T16, Time T26, and Time T36.

In FIG. 8A to FIG. 8C, images at different times after Time T14, Time T24, and Time T34 at which the feature extraction unit 30 detects the end of eye blinking are stored as Data 1, Data 2, and Data 3.

FIG. 8A shows an example in which the white part of the eye oscillates in the lateral direction. The oscillation width of the white part of the eye can be easily detected in the case where the white part of the eye oscillates in the x-axis direction.

FIG. 8B shows an example in which the white part of the eye oscillates in an oblique direction. In the case where the white part of the eye oscillates in the oblique direction, the oscillation width of the white part of the eye can be detected by converting the oscillation in the oblique direction into the oscillation in the x-axis direction. Note that in the case where the oscillation in the oblique direction is determined, the white area may be further divided by the y-coordinate of the center coordinates C(a, b) so that the areas of the four areas of the white area 101A to a white area 101D can be compared. This can reduce processing for detecting the amount of movement in the oblique direction or the like, reducing power consumption.

FIG. 8C shows a case where the eyelid moves up and down. Since this is difficult to detect from the area ratio of the white part of the eye, the blinking amplitude y is preferably detected. In the case where the white part of the eye moves in the x-axis direction or the oblique direction in FIG. 8C, the fluctuation width of the white part of the eye can be easily detected. A combination with the oscillation width of the white part of the eye allows a more accurate classification of person's conditions.

Figure 9:
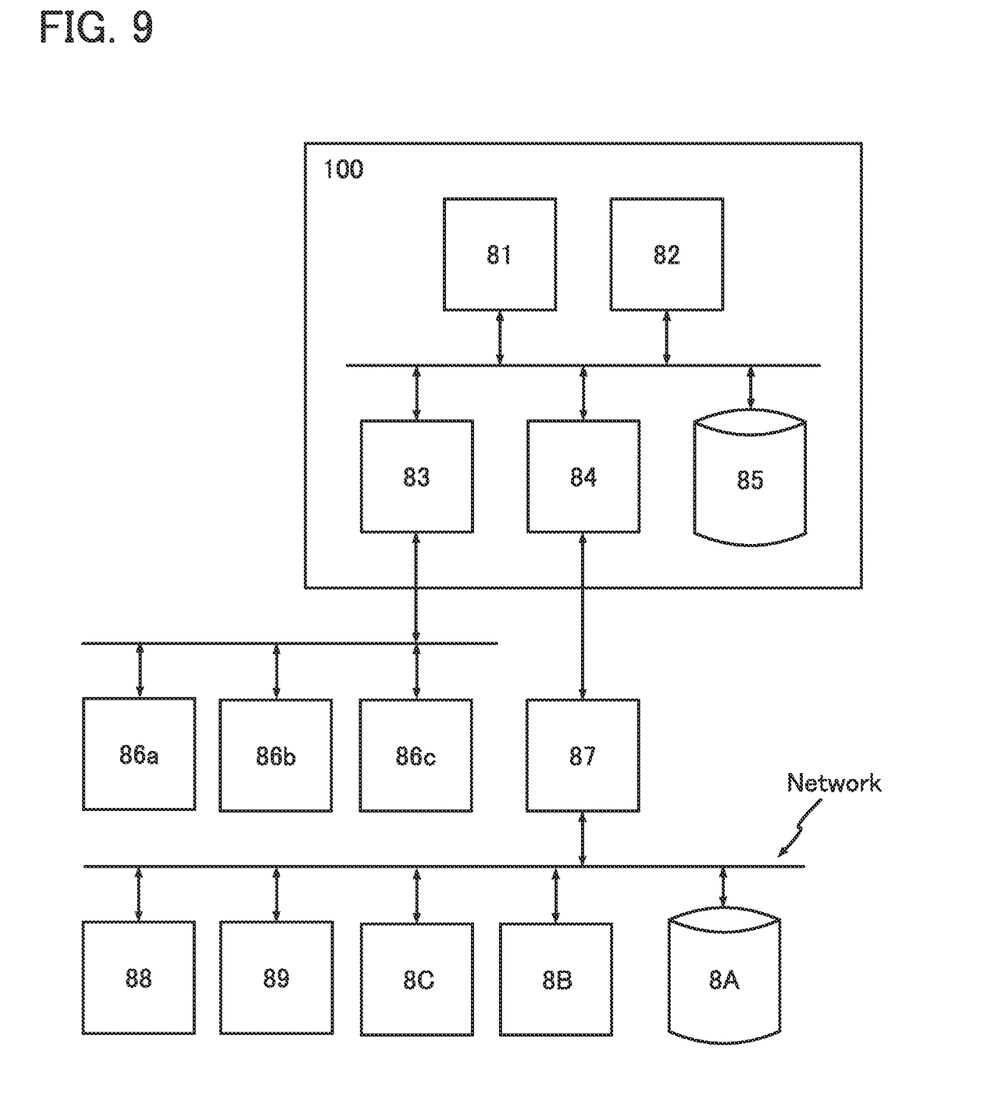
FIG. 9 is a block diagram illustrating a classification device.

FIG. 9 is a block diagram illustrating a classification device 100 provided with a method for classifying person's conditions according to eye data.

The classification device 100 includes an arithmetic unit 81, a memory 82, an input/output interface 83, a communication device 84, and a storage 85. The method for classifying person's conditions according to eye data by the classification device 100 is provided by a program including the imaging device 20, the feature extraction unit 30, and the feature estimation unit 40. Note that the program is stored in the storage 85 or the memory 82, and parameter search is performed using the arithmetic unit 81.

A display device 86a, a keyboard 86b, a camera 86c, and the like are electrically connected to the input/output interface 83. Although not shown in FIG. 9, a mouse or the like may be connected.

The communication device 84 is electrically connected to another network through a network interface 87. Note that the network interface 87 includes wired or wireless communication. A monitoring camera 88, a Web camera 89, a database 8A, a remote computer 8B, a remote computer 8C, and the like are electrically connected to the network. Note that the monitoring camera 88, the Web camera 89, the database 8A, the remote computer 8B, and the remote computer 8C that are electrically connected through the network may be placed in different buildings, different regions, or different countries.

The structures and the methods shown in one embodiment of the present invention can be partly used in an appropriate combination.

REFERENCE NUMERALS

:Data 1: data, Data 2: data, Data 3: data, T1: time, T2: time, T3: time, T4: time, T5: time, T6: time, T11: time, T12: time, T13: time, T14: time, T15: time, T16: time, T17: time, T21: time, T22: time, T23: time, T24: time, T25: time, T26: time, T27: time, T31: time, T32: time, T33: time, T34: time, T35: time, T36: time, T37: time, y1: blinking amplitude, y2: blinking amplitude, y3: blinking amplitude, 8A: database, 8B: remote computer, 8C: remote computer, 10: classification device, 20: imaging device, 21a: image, 21n: image, 22: image, 22a: image, 22n: image, 22p: image, 22q: image, 22r: image, 30: feature extraction unit, 31: eye blinking detection unit, 32: memory control unit, 33: storage unit, 33a: storage device, 33b: storage device, 34: detection unit, 35: data detection unit, 40: feature estimation unit, 40a: classifier, 41: teacher data, 81: arithmetic unit, 82: memory, 83: input/output interface, 84: communication device, 85: storage, 86a: display device, 86b: keyboard, 86c: camera, 87: network interface, 88: monitoring camera, 89: Web camera, 100: classification device, 101: white area, 101A: white area, 101B: white area, 102: pupil, 102a: black area, 103: iris, 104: eyelid

The invention claimed is:

1. A classification method using an imaging device, a feature extraction unit, and a classifier,
wherein the classifier comprises a classification model,
wherein the imaging device has a function of generating a group of images by continuous image capturing,
wherein the group of images comprises an image of an eye area,
wherein the eye comprises a white area,
wherein the white area is an area in which an eyeball is covered with a white coating,
wherein the classification method comprises the steps in which the feature extraction unit extracts the eye area from the group of images, extracts a blinking amplitude from the group of images, detects an image for determining start of eye blinking from the group of images, stores an image for determining end of eye blinking from the group of images as first data, and stores an image after a predetermined time elapsed from the first data from the group of images as second data,
wherein the classification method comprises the step in which the feature extraction unit extracts area data of the white area from the first data and the second data,
wherein the classification method comprises the step in which the feature extraction unit supplies the area data of the white area to the classifier as learning data, and
wherein the classification method comprises the step in which the classifier generates the classification model using the learning data.

2. The classification method according to claim 1,
wherein the images of the eye areas included in the first data and the second data each include the white area,
wherein in the case where the detected area data of the white area comprises a first area and a second area independently, the classification method comprises the step in which the feature extraction unit outputs a ratio between the first area and the second area,
wherein in the case where the detected area data of the white area is detected as a third area, the classification method comprises the steps in which the feature extraction unit detects a circle area from the third area, obtains a center of the circle from the circle area, divides the third area into the first area and the second area using an x-coordinate of the center of the circle, and outputs the ratio between the first area and the second area,
wherein the classification method comprises the step in which the feature extraction unit calculates an oscillation width of a white part of the eye from the ratio between the first area and the second area, and
wherein the classifier uses the oscillation width of the white part of the eye as the learning data.

3. The classification method according to claim 1, comprising:
the step in which the feature extraction unit supplies the oscillation width of the white part of the eye and the blinking amplitude as the learning data to the classifier; and
the step in which the classifier generates the classification model using the oscillation width of the white part of the eye and the blinking amplitude.

4. The classification method according to claim 1, comprising:
the step of training the classifier using the learning data;
the step of supplying new first data and new second data to the feature extraction unit; and
the step in which the classifier classifies person's emotional or physical conditions using the classification model.

5. The classification method according to claim 1, comprising:
the step of attaching a teacher label to the learning data, and
the step in which the classifier trains the classifier using the learning data to which the teacher label is attached.

* * * * *